United States Patent [19]

Bark et al.

[11] Patent Number: 4,908,029
[45] Date of Patent: Mar. 13, 1990

[54] FLEXIBLE NEEDLE STOP

[75] Inventors: Jeffrey E. Bark; Keith A. Young, both of Racine, Wis.

[73] Assignee: Medical Engineering Corporation, Racine, Wis.

[21] Appl. No.: 343,098

[22] Filed: Apr. 25, 1989

[51] Int. Cl.$^4$ ................................................ A61F 2/12
[52] U.S. Cl. ........................................ 623/8; 128/894; 604/93
[58] Field of Search ............... 604/93; 128/899; 623/8

[56] References Cited

U.S. PATENT DOCUMENTS

| | | | |
|---|---|---|---|
| 4,190,040 | 2/1980 | Schulte | 623/8 |
| 4,543,088 | 9/1985 | Bootman | 604/93 |
| 4,685,447 | 8/1987 | Iversen | 128/899 |
| 4,840,615 | 6/1989 | Hancock | 128/899 |

Primary Examiner—Richard J. Apley
Assistant Examiner—James Prizant
Attorney, Agent, or Firm—Stuart E. Krieger

[57] ABSTRACT

The flexible needle stop includes a normally unfolded needle impenetrable needle barrier formed of a flexible foldable material. The flexible foldable material can be a single layer sheet material, a wire mesh material and/or one or more layers of scale-like components arranged side by side. The scale-like components are physically unconnected and of a size that permits flexion of the needle stop that incorporates the scale-like components. The flexible needle stop member can include a bead-like periphery which affords the needle stop member with a resilient memory and helps restore the needle stop member to its normally unfolded condition after a folding restraint is removed. The needle stop can be freely disposed within a fill chamber of a tissue expander, attached to an inner surface of the fill chamber or incorporated in the shell wall of a tissue expander.

36 Claims, 8 Drawing Sheets

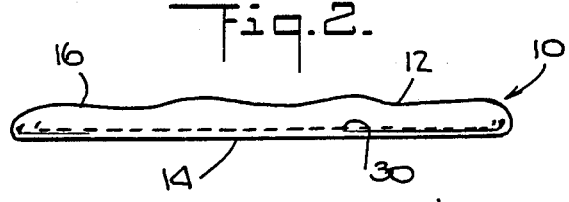
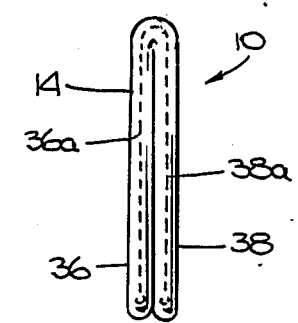
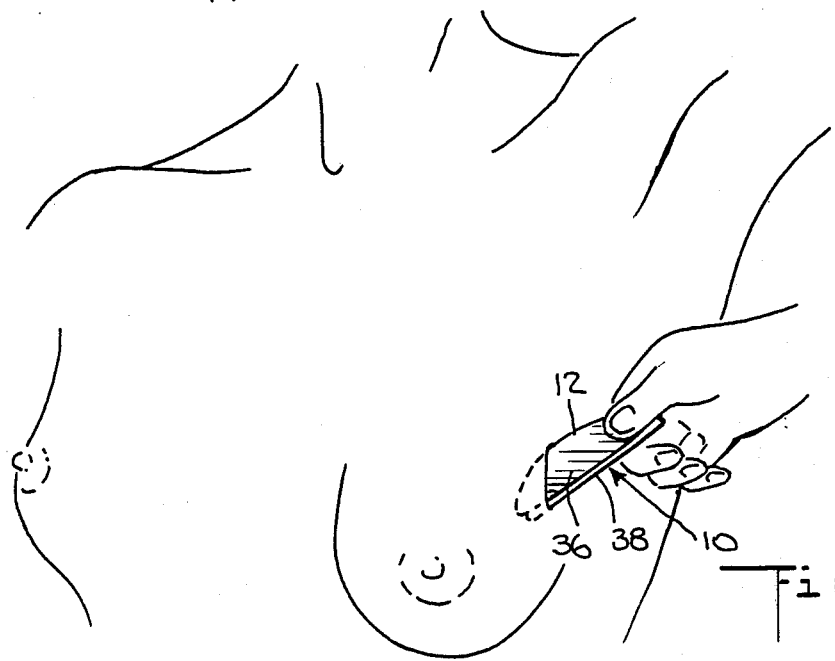

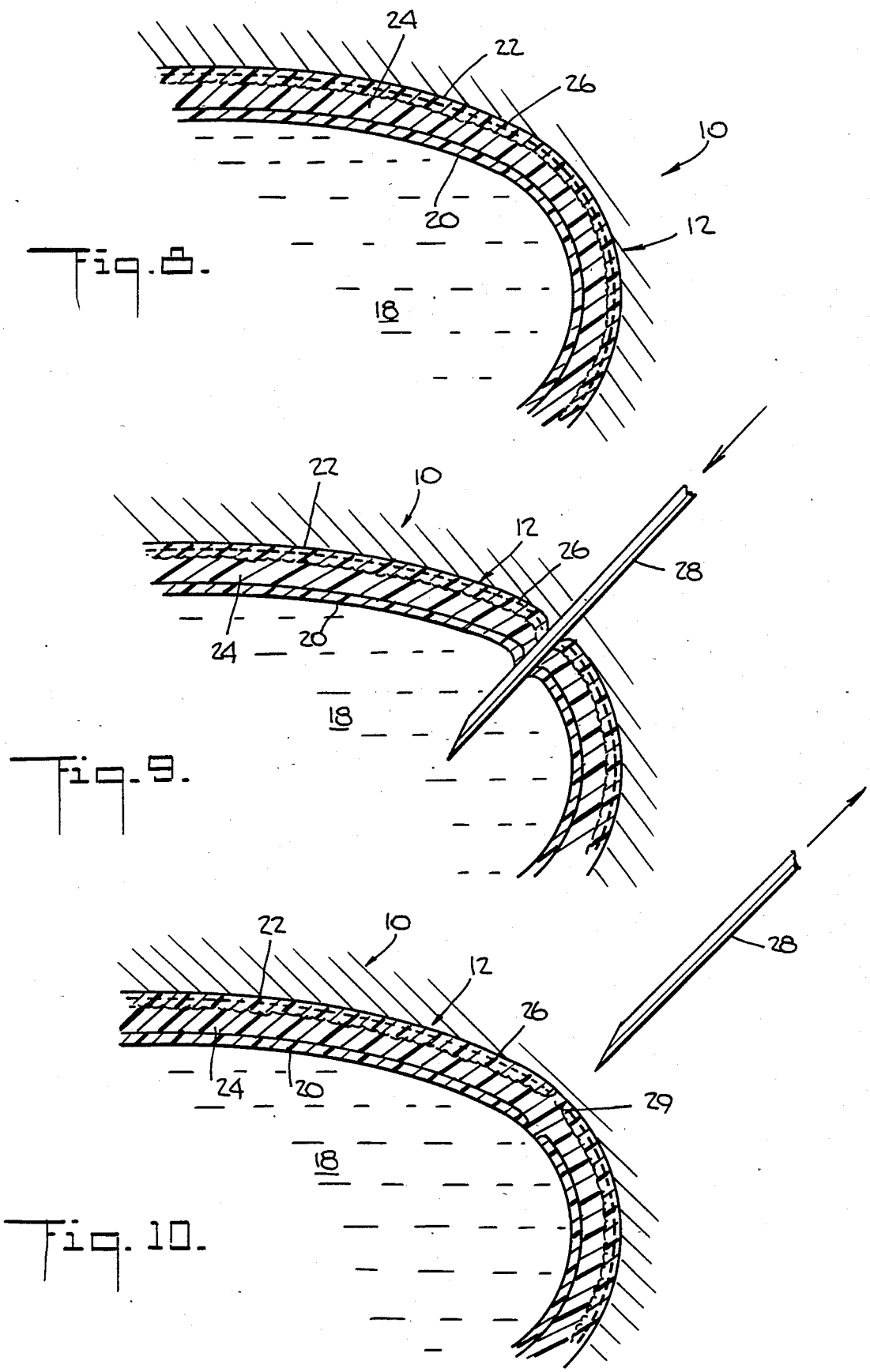

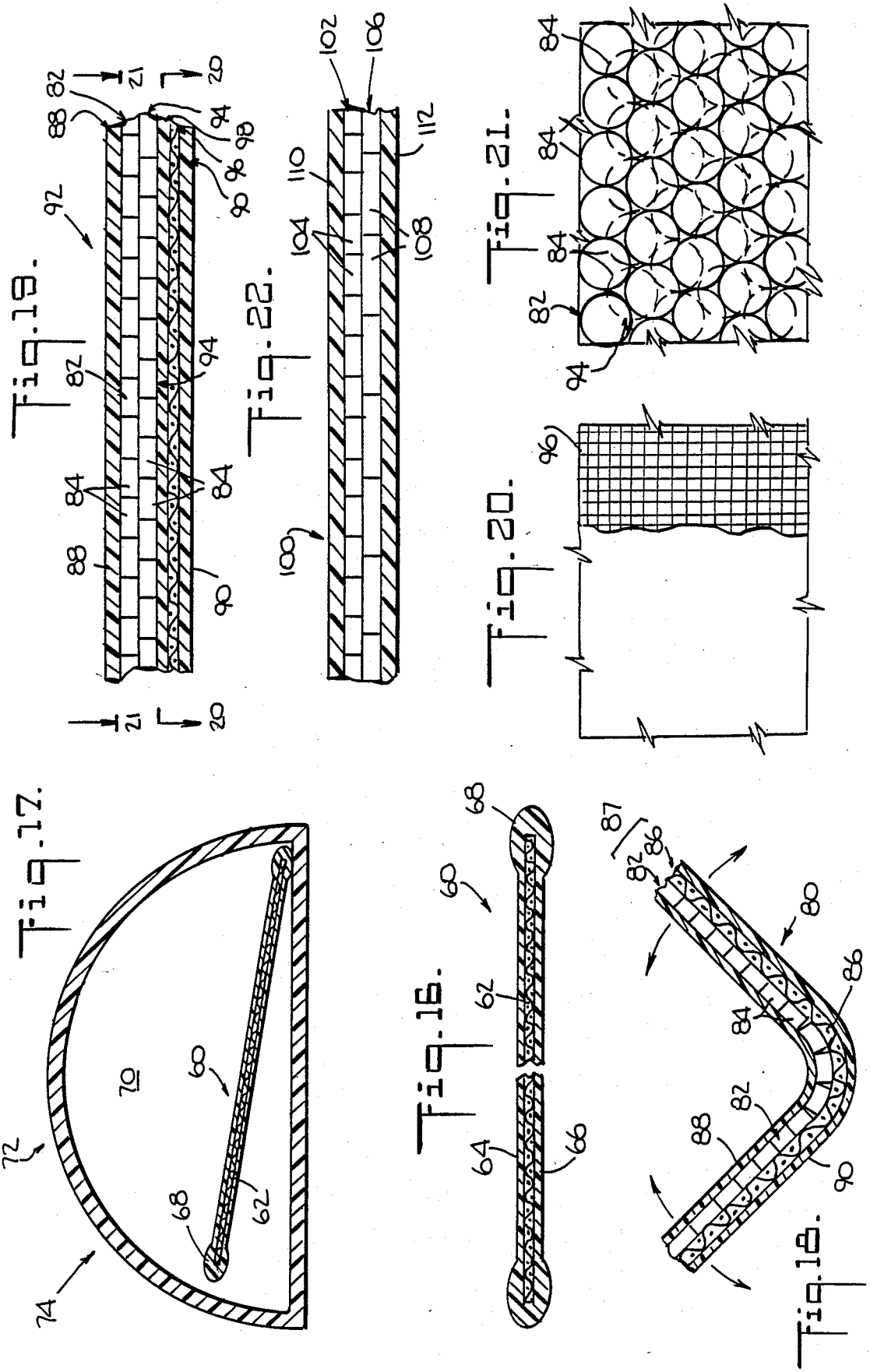

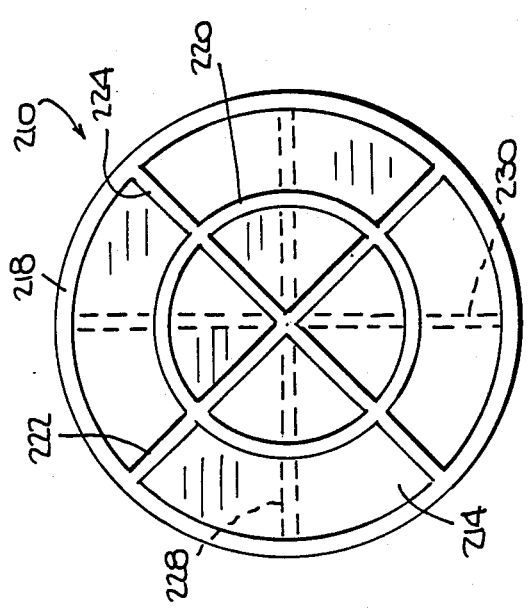
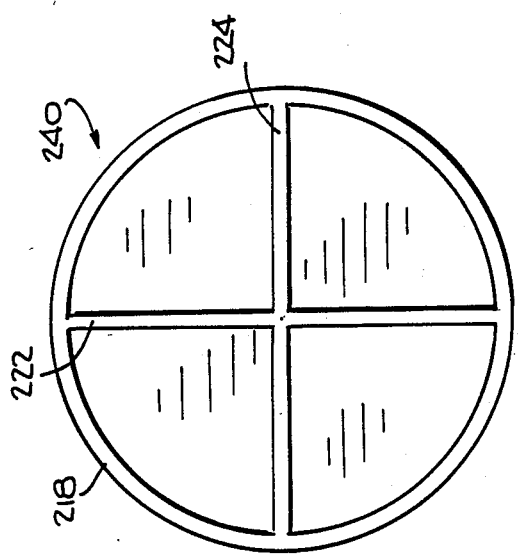
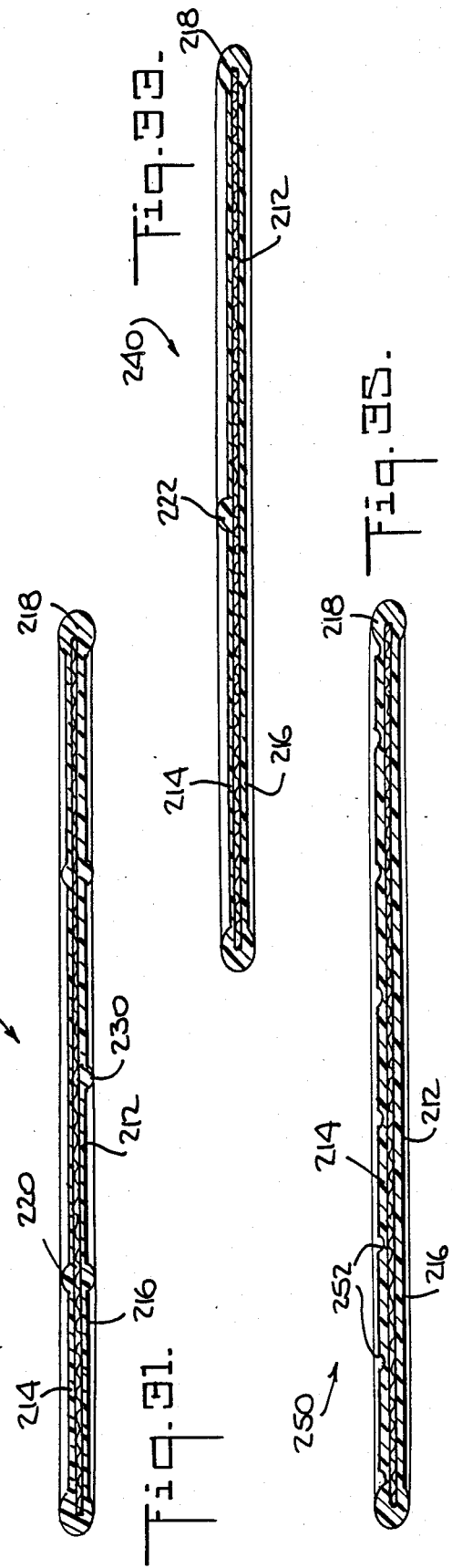

FLEXIBLE NEEDLE STOP

BACKGROUND OF THE INVENTION

This invention relates to implantable devices for promoting tissue growth or tissue expansion, and more particularly to a flexible, foldable needle stop device for a fluid expandable prosthesis.

Tissue expander prostheses are generally used to promote tissue growth by gradually expanding the prosthesis beneath the skin in an area where tissue growth is desired. The prosthesis is typically a collapsible shell formed of a flexible, foldable material which establishes a fluid chamber. Infusion of fluid in the fluid chamber expands the prosthesis to promote tissue growth.

Infusion of fluid into a tissue expander prosthesis is normally accomplished with an infusion needle. Since a tissue expander shell is likely to leak if punctured by a needle, it is common practice to use a tissue expander system that includes resealable septums such as shown in U.S. Pat. Nos. 4,190,040; 4,463,733; and 4,543,088.

Septums are relatively inflexible, non-expandable, infusible hollow structures that enable fluid to flow into a tissue expander structure once the inner capacity of the septum is filled. As shown in the foregoing patents, the septum is connected to a tissue expander structure by a conduit such that fluid infused into the septum is directed by the conduit into the tissue expander chamber. Septums usually have the capability of being resealable when an injection needle is withdrawn.

Known tissue expansion systems often require implantation of a septum, a tissue expander prosthesis and the conduit that connects the septum to the tissue expander prosthesis. The surgery for implanting a tissue expansion system normally includes an incision or incisions through which the implant is directed and a surgical pocket for accommodating the implant. The size of the implantation incision and pocket is generally based upon the size of the respective components of the tissue expander system.

In an attempt to simplify tissue expansion systems and reduce the size of implantation incisions and surgical pockets, a self-sealing tissue expander device has been developed and is the subject of a co-pending patent application. The self-sealing tissue expander device eliminates the need for a septum and the connection tube that normally connects the septum to the tissue expander. As a result, the implantation incision and the surgical pocket needed for implanting the self-sealing tissue expander need only be of sufficient size to accommodate the tissue expander, since there is no accompanying septum and connection tube.

When a self sealing tissue expander of the type previously referred to is used without a septum, it is desirable to provide a needle stop device therein. Needle stop devices are usually rigid, impenetrable structures that resist needle penetration and block further passage of a needle beyond the location of the needle stop. The needle stop device prevents an infusion needle that has entered the infusion chamber of the tissue expander device from passing beyond the chamber through the tissue expander shell. The needle stop device ideally is of a size and shape which does not obstruct entry of a needle into the fluid chamber but is of sufficient size to prevent through passage of the needle beyond the chamber.

Implantation of a tissue expander prosthesis is normally carried out with the prosthesis in an unexpanded or substantially empty condition, wherein the shell can be folded or otherwise compacted to the smallest practical size to minimize the incision needed to accomplish implantation. However, in tissue expander devices which include needle stops, the smallest practical compaction of the tissue expander is usually determined by the size of the relatively rigid needle stop device. Therefore, the minimum size of the implantation incision often corresponds to the size of the needle stop device.

It is thus desirable to provide a flexible, foldable needle stop structure for a tissue expansion device that enables the tissue expansion structure, along with the needle stop structure to be folded or otherwise reduced in size for implantation through an incision of minimal size.

OBJECTS AND SUMMARY OF THE INVENTION

Among the several objects of the present invention may be noted the provision of a novel flexible, foldable needle stop device for a tissue expander prosthesis, a novel tissue expander prosthesis containing a flexible, foldable needle stop, a novel tissue expander prosthesis which includes a needle stop that can be folded and reduced in size along with the shell of the tissue expander prosthesis, a novel flexible, foldable tissue expander prosthesis which includes a needle stop structure that is also flexible and foldable and can be located in any desired position within the shell of the tissue expansion device, and a novel method of expanding tissue.

Other objects and features of the invention will be in part apparent and in part pointed out hereinafter.

In accordance with the present invention, the flexible needle stop includes a manually flexible needle impenetrable barrier suitable for disposition in a tissue expander that is preferably a self-sealing tissue expander. The needle impenetrable barrier, in one embodiment of the invention, includes a sheet of needle impenetrable material of predetermined thickness to provide flexibility. The needle stop is formed with a peripheral bead which promotes restoration of the needle impenetrable barrier to a normally unfolded condition after it has been folded.

The flexible needle stop can be freely disposed in a fill chamber of a tissue expander, attached to a surface portion of the fill chamber or embedded in the wall of the tissue expander.

In another embodiment of the invention the flexible needle stop includes a wire mesh material of sufficiently small gauge and mesh to form a flexible needle impenetrable barrier. The wire mesh material can be layered with plastic and provided with a peripheral bead for free disposition in the fill chamber of a tissue expander. One or both plastic layers can be reinforced to promote quick return of the needle stop to the flat position after deformation.

In another embodiment of the invention at least one plastic layer can be grooved in the manner of a living hinge to enhance and facilitate foldability of the flexible needle stop.

The flexible needle stop incorporating the wire mesh material can also be adhered to a surface of the fill chamber or the wire mesh material can be incorporated in the wall of the shell material constituting the tissue expander.

Other embodiments of the invention include a plurality of scale-like members arranged side by side to form a layer. The layer of scale-like members can be backed up by a layer of wire mesh material such that the combination of the layer of scale-like members and the layer of wire mesh material form a needle impenetrable needle stop barrier.

Still other embodiments of the invention include more than one layer of scale-like members wherein one layer of scale-like members is offset from the other layer. A further embodiment includes scale-like members of one size in one layer and scale-like members of another size in another layer. The multiple layers of scale-like members can be backed up by a layer of wire mesh material. As a further alternative, the layer(s) of scale-like members and the layer of wire mesh material can be embedded in a portion of the tissue expander shell.

Further embodiments of the invention include scale-like members of different size in a single layer yet placed side by side in unconnected relationship. The layer of scale-like members of different size can also be backed up by a layer of wire mesh material to form a needle impenetrable needle barrier. The needle impenetrable needle barrier can, as previously described, be layered with plastic material and provided with a peripheral bead for free disposition in a tissue expander fill chamber. Alternatively, the needle impenetrable needle barrier can be incorporated in the shell of the tissue expander.

Still another embodiment of the invention includes a layer of scale-like members of different complementary shapes which are arranged to fit side by side without physical connection. The different shaped scale-like members can also be backed up by a layer of wire mesh material such that the combination of layers forms a needle impenetrable needle barrier. The needle impenetrable needle barrier can be layered with plastic and provided with a peripheral bead or incorporated in the shell of a tissue expander.

In each of the embodiments that include similar or dissimilar shaped scale-like members placed side by side in close proximity, complementary shaped beveled edges or a combination of complementary shaped beveled edges and recesses can be included in the peripheries of the members. Such provision permits overlapping of the individual scale-like members to minimize or eliminate actual or potential gaps between adjacent members. A wire mesh backup for any of the multi-component layers of unattached members helps assure the needle impenetrability of the needle barrier.

The invention accordingly comprises the constructions and method hereinafter described, the scope of the invention being indicated in the claims.

DESCRIPTION OF THE DRAWINGS

FIG. 1 is a simplified pictorial view showing a tissue expansion device prior to folding and implantation with a flexible needle stop incorporating one embodiment of the invention;

FIG. 2 is an enlarged simplified schematic elevational view thereof in an unfolded, unexpanded condition;

FIG. 3 is a simplified pictorial view thereof in a folded condition during implantation;

FIG. 4 is an enlarged simplified schematic view thereof in a folded condition;

FIGS. 8-10 are enlarged fragmentary details of the tissue expander shell before, during and after infusion;

FIG. 16 is an enlarged fragmentary sectional view of a needle stop incorporating another embodiment of the invention;

FIG. 17 is a sectional view of a tissue expander incorporating the needle stop of FIG. 16;

FIG. 18 is an enlarged fragmentary sectional view of a needle stop incorporating a further embodiment of the invention;

FIG. 19 is an enlarged fragmentary sectional view of a needle stop incorporating another embodiment of the invention;

FIG. 20 is a sectional view taken on the line 20—20 of FIG. 19;

FIG. 21 is a sectional view taken on the line 21—21 of FIG. 19;

FIG. 22 is an enlarged fragmentary sectional view of a flexible needle stop incorporating still another embodiment of the invention;

FIG. 30 is a plan view of a needle stop incorporating another embodiment of the invention;

FIG. 31 is an enlarged simplified sectional view thereof;

FIG. 32 is a plan view of a needle stop incorporating still another embodiment of the invention;

FIG. 33 is an enlarged simplified sectional view thereof;

FIG. 34 is a plan view of a still further embodiment of the invention; and,

FIG. 35 is an enlarged simplified sectional view thereof. Corresponding reference characters indicate corresponding parts throughout the several views of the drawings.

DETAILED DESCRIPTION OF THE INVENTION

A tissue expander device incorporating one embodiment of the flexible needle stop is generally indicated by the reference number 10 in FIG. 1.

Figure 11:
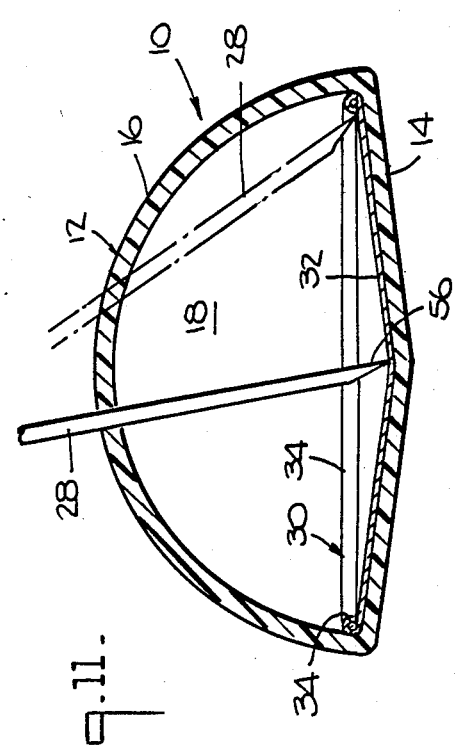
FIG. 11 is an enlarged simplified sectional view thereof showing the flexible, foldable impenetrable characteristics of the needle stop during infusion.

Referring to FIG. 11, the tissue expander 10, which can be of any selected shape, includes a shell 12 having a base portion 14 and a dome-shaped (when expanded) promontory portion 16 joined to the base portion 14 to define a fill chamber 18. The shell 12 is formed of a suitable biocompatible elastomeric material such as polydimethylsiloxane.

Referring to FIG. 8, the shell 12 is preferably a self-sealing structure of the type disclosed in a co-pending patent application. For example, the shell 12 includes inner and outer elastomeric layers 20 and 22 which can be formed, for example, of polydimethylsiloxane with a Durometer of approximately 35 Shore A. The layers 20 and 22 sandwich an interior layer 24 which can be formed, for example, of polydimethylsiloxane with a Durometer of approximately 2 Shore A. If desired, a layer 26 of Dacron mesh can be embedded in the layer 22 in any suitable known manner. The layers 20 and 22 can be approximately 0.015 inches thick and the layer 24 can be approximately 0.040 inches thick.

Under this arrangement, and referring to FIGS. 8–10, the shell 12 will reseal a needle entry puncture 29 (FIG. 10) caused by a hypodermic needle 28, such as a 21 gauge needle.

Figure 12:
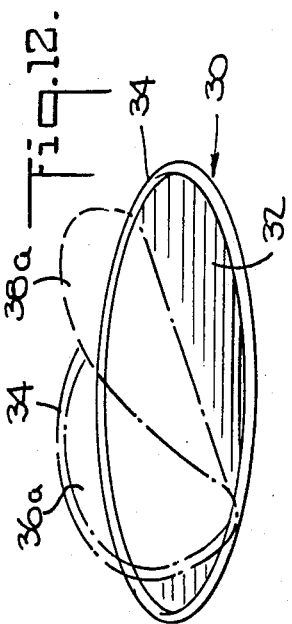
FIG. 12 is a simplified schematic view of the needle stop showing, in dotted outline, a portion of the range of foldability thereof.

Referring to FIGS. 11–12, the tissue expander 10 includes a needle stop 30 having a peripheral shape that substantially corresponds to the shape of the base portion 14. The needle stop 30, which is formed of a needle-impenetrable, non-corrosive material such as titanium or stainless steel, includes a main barrier section 32 of substantially uniform thickness, for example, approximately 0.002 inches, and a rolled peripheral edge or bead portion 34 which can have a roll diameter of approximately 0.060 inches. The overall diameter of the needle stop 30, for a tissue expander with a circular base portion 14, can be, for example, approximately 4 inches.

The needle stop 30 can be freely disposed in the chamber 18 in the orientation shown in FIG. 11 or adhered to the base portion 14 preferably with a silicone adhesive such as the room temperature vulcanizing type.

Figure 13:
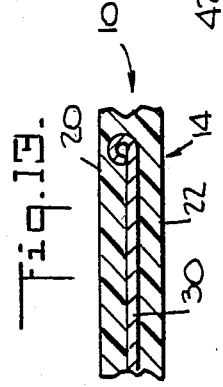
FIG. 13 is an enlarged fragmentary sectional view of the needle stop wherein the needle stop is sandwiched within the shell wall of the tissue expander.

The phrase "freely disposed" as used herein is intended to mean unattached to any part of the tissue expander 10. If desired, the needle stop 30 can be sandwiched in the base portion 14 in the manner shown in FIG. 13. Thus at the base portion 14, the needle stop 30 is embedded between the inner layer 20 and the outside layer 22.

The phrase "within the shell" as used herein is intended to mean the location of a needle stop structure anywhere in the confines of the shell structure including in the fill chamber, on any portion of the shell wall inside the fill chamber, or sandwiched in any portion of the shell wall.

In using the tissue expander 10, the fill chamber 18 is substantially empty prior to implantation. The shell 12 and the needle stop 30 can thus be compacted or folded from the configuration of FIGS. 1 and 2 to the configuration of FIGS. 3 and 4 wherein the tissue expander 10 is characterized by folded over portions 36 and 38. A portion of the range of foldability of the needle stop 30 is illustrated in FIG. 12. The needle stop 30 thus includes corresponding folded over portions 36a and 38a.

Folding or compaction of the tissue expander 10 helps minimize the size of an implantation incision 40 (FIG. 1) needed for implantation of the tissue expander 10. After the tissue expander 10 has been implanted in a patient, and the folding force is released, the needle stop 30 will substantially unfold to the normally unfolded condition due to the flexibility of the main section 32 and the resiliency of the bead portion 34, which affords the needle stop 30 with a memory that assures substantial unfolding of the needle stop 30 after the folding force is released therefrom.

Figure 15:
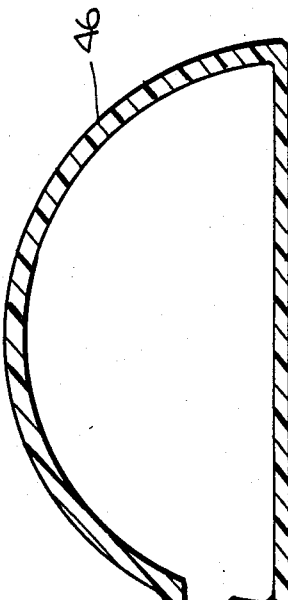
FIG. 15 is an enlarged sectional view thereof.
Figure 14:
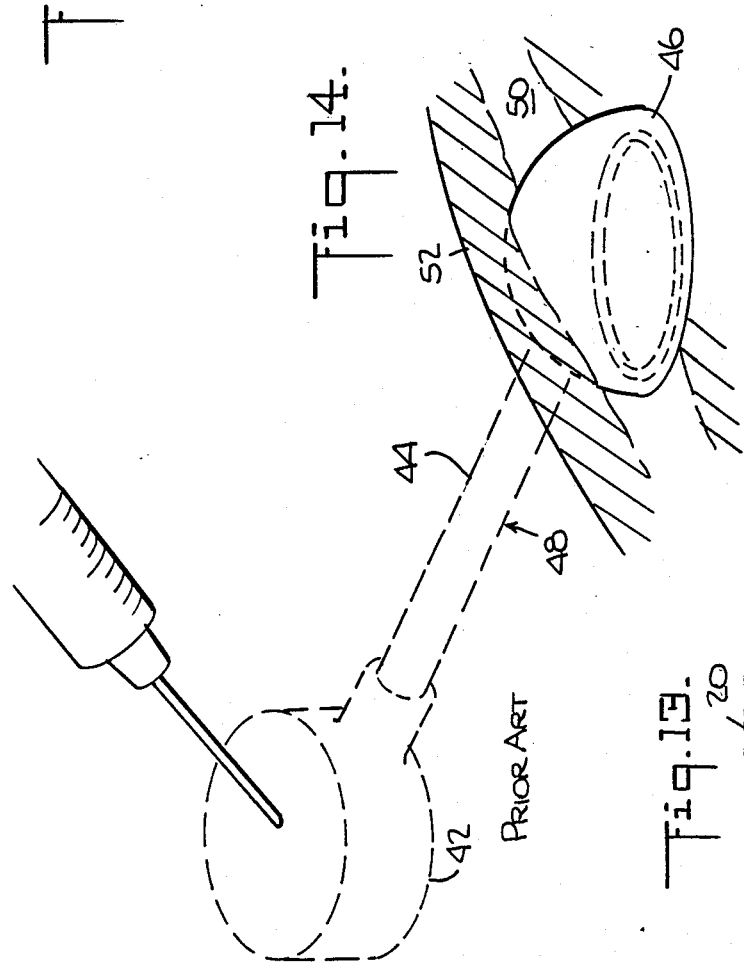
FIG. 14 is a perspective view of a prior art device.

Prior art tissue expansion devices of the type shown in FIGS. 14 and 15 included a fill port or septum 42, a connection tube 44 and a tissue expander 46 which constitute a tissue expansion system 48. The tissue expander 46 is thus remotely filled by fluid infusion through the septum 42. In order to implant the tissue expansion system 48, a tunnel or pocket 50 (FIG. 14) must be created through subcutaneous tissue 52 to accommodate the septum 42, the connection tube 44 and the tissue expander 46. The high degree of surgical skill needed for such implantation as well as the potential complications and discomfort for a patient represent potential problems that are addressed by this invention since the septum and connection tube are eliminated, and the tissue expander can be compacted to minimize the implantation incision.

The incision 40 for the tissue expander 10 can thus be of substantially less size and scope than the incision needed to implant prior art devices. After the tissue expander 10, which incorporates the present invention, is implanted in the incision 40, infusion can begin.

Figure 6:
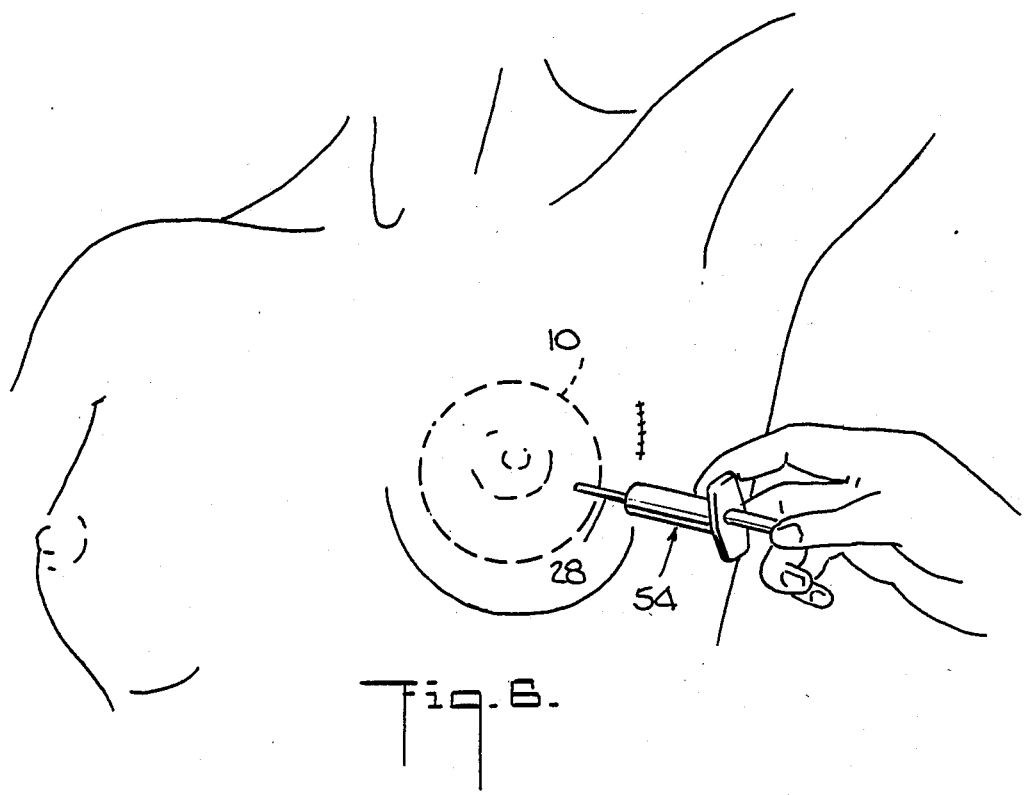
FIG. 6 is a simplified schematic pictorial front view showing the manner in which the tissue expander device is infused with fluid.
Figure 7:
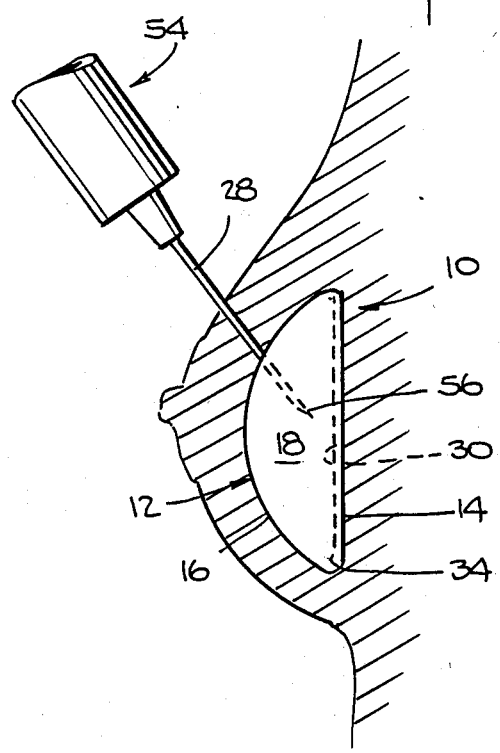
FIG. 7 is a side view thereof during infusion.

Referring to FIGS. 6 and 7, the tissue expander 10, in its substantially empty condition, is oriented in a manner wherein the needle stop 30 has a proximal location. A syringe 54 including the hypodermic needle 28 is directed toward the tissue expander 10 which is generally located using palpation procedures. The needle 28 is directed into the tissue expander 10, penetrating the promontory portion 16 of the shell 12 and entering the chamber 18. The needle 28 is directed toward the base 14 of the tissue expander 10 such that a point 56 (FIG. 7) of the needle 28 can bottom against the needle stop 30.

The needle stop 30 thus prevents the needle 28 from passing out of the chamber 18 once it is directed into the chamber 18 for infusion purposes. The bead portion 34 of the needle stop 30, in addition to affording the needle stop with a predetermined resiliency, also functions to limit movement of the needle point 56 beyond the bead 34.

Deflections of the needle stop 30 by the needle 28 during infusion, due to flexibility of the needle stop 30, will substantially self correct when needle pressure is removed from the needle stop 30. The needle stop 30 is thus restorable to a substantially unfolded, undeflected condition by the resiliency of the needle stop 30 and the memory of the rolled edge or bead 34.

Figure 5:
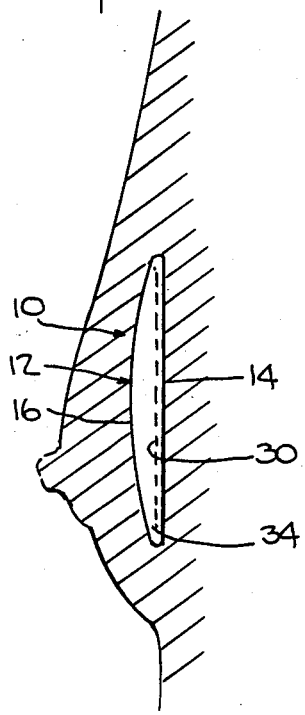
FIG. 5 is a sectional view thereof after implantation.

Infusion of fluid into the chamber 18 enables the tissue expander 10 to expand from the substantially empty condition f FIG. 5 to the substantially filled condition of FIG. 7, over a series of periodic fluid infusions.

When an individual infusion operation is completed, the needle 28 is withdrawn and the tissue expander shell 12 self seals in the manner shown in FIGS. 9 and 10. The middle layer 24 deforms and flows under a compressive force provided by the inner and outer layers 20 and 22 to seal the puncture 29 caused by the needle 28 in the inner and outer layers 20 and 22.

A flexible needle stop incorporating another embodiment of the invention is generally indicated by the reference number 60 in FIG. 16. The needle stop 60 comprises a wire mesh insert 62, which can be formed of stainless steel. A number 80 mesh having a 0.0055 inch wire diameter has been found adequate. A plastic material such as a silicone elastomer is molded over each side of the mesh to form layers 64 and 66. The thickness of each layer 64 and 66 can be approximately 0.02 inches. A plastic bead 68 is formed at the periphery of the insert 62 as a continuation of the layers 64 and 66. The bead 68 can be approximately 0.156 inches thick and 0.250 inches wide.

The flexible needle stop 60 can be of any selected shape such as a circular shape for example to correspond to the general shape of the tissue expander in which the needle stop is disposed. For example, referring to FIG. 17, a generally circular flexible needle stop 60 is freely disposed in the chamber 70 of a tissue expander 72 having a shell portion 74 that is identical in construction with the shell portion 12 of the tissue expander 10.

The tissue expander 72 with the flexible needle stop 60 is used in a manner similar to that previously described for the tissue expander 10. Thus the tissue expander shell portion 74 and the needle stop 60 can be folded or compacted prior to implantation in the manner shown in FIG. 4, for example, to minimize the size of the implantation incision. After the tissue expander 72 is implanted, the needle stop 60, when free of restraint, will substantially resume the unfolded condition as shown in FIGS. 16 and 17. The bead portion 68 functions to help restore the unfolded condition of the needle stop 60 when it is free of restraint.

Although the shell portion 74 is shown in simplified schematic form, it includes the various layers described in connection with FIG. 8. Accordingly, the needle stop 60 will prevent a needle (not shown) that penetrates the tissue expander shell portion 74 for infusion of fluid into the chamber 70 from passing beyond the chamber 70. Furthermore, when the needle is withdrawn from the chamber 70, the needle entry puncture in the shell portion 74 will reseal in the manner previously described for the shell 12.

Since the tissue expander 72 is a self-sealing device, there is no need to use a septum or a connecting tube to infuse fluid into the chamber 70. Accordingly, the size of the implantation incision is substantially reduced by the absence of such components, and is reduced even further by virtue of the foldability and resiliency of the needle stop.

Another embodiment of the flexible needle stop is generally indicated by the reference number 210 in FIGS. 30 and 31. The needle stop 210 includes a wire mesh insert 212, plastic layers 214 and 216 and a peripheral bead 218 which respectively correspond to the wire mesh insert 62, the plastic layers 64, 66 and the peripheral bead 68 of the needle stop 60.

The layer 214 is formed with a rib-like generally circular reinforcement 220 and rib-like linear reinforcements 222 and 224 that criss-cross each other at an approximate 90° angle and intersect at the approximate center of the circular reinforcement 220. The layer 216 is similarly reinforced with a rib-like circular reinforcement 226 and rib-like linear reinforcements 228 and 230. However the linear reinforcements 228 and 230 are offset approximately 45° from the linear reinforcements 222 and 224. The reinforcements 220-230 can be approximately 0.1875 inches thick and project approximately 0.0625 inches from the respective layers 214 and 216.

Under this arrangement the reinforcements 220-230 are sufficiently flexible to permit easy bending of the needle stop 210 and promote the quick return of the needle stop 210 to the flat position after deformation or folding. The flexible needle stop 210 can be freely disposed in or otherwise incorporated in a tissue expander such as the tissue expander 10 or 72, and used in a manner similar to that previously described for the needle stops 30 and 60.

A further embodiment of the flexible needle stop is generally indicated by the reference number 240 in FIGS. 32 and 33. The needle stop 240 includes the wire mesh insert 212, plastic layers 214 and 216, the peripheral bead 218 and the linear reinforcements 222 and 224 that criss-cross each other at an approximate 90° angle. If desired the layer 216 can be provided with corresponding reinforcements depending upon the specific application of the tissue expander.

As will be noted from a comparison of the tissue expanders 10 and 240, one or both layers of the needle stop can be reinforced to promote a relatively quick return of the needle stop to the flat position after deformation or folding. The needle stop 240 is used in a manner similar to that described for the needle stop 210.

Another embodiment of the flexible needle stop is generally indicated by the reference number 250 in FIGS. 34 and 35. The needle stop 250 includes the wire mesh insert 212, the plastic layers 214 and 216, and the peripheral bead 218. A grid-like pattern of grooves 252 is formed in the layer 214, approximately 0.1875 inches wide and 0.0625 inches deep.

The grooves 252 are functionally similar to living hinges to enhance and facilitate bending of the flexible needle stop. Multiple bends can be developed along several respectively spaced grooves, and intersecting bends can also be utilized to fold the flexible needle stop 250 into the smallest possible configuration during implantation of a tissue expander containing the needle stop.

If desired, the flexible needle stop 250 can be provided with as few as one groove 252. Although not shown, one or more corresponding aligned grooves 252 can also be formed on the layer 216.

The flexible needle stop 250 can be freely disposed in or otherwise incorporated in a tissue expander such as the tissue expander 10 or 72 and used in a manner similar to that previously described for the needle stops 30 and 60.

Another embodiment of a flexible needle stop is generally indicated by the reference number 80 in FIG. 18. The needle stop 80 includes a layer 82 of relatively small scale-like members such as metal disks 84 which can be formed, for example, of stainless steel. The disks 84, which can be of circular shape, are placed side by side in abutting relationship in a manner similar to that shown in solid lines in FIG. 21. The disks 84 are not connected to each other and thus have the potential to move independently of one another to afford flexibility to the layer 82.

To help prevent passage of a needle point between the disks, the edges of individual disks can be beveled and arranged in the manner shown in FIG. 30 such that one disk overlaps another without being firmly affixed to one another. The disks 84 which form the layer 82 can be approximately 0.25 inches in diameter and 0.015 inches thick.

Whether or not the disks 84 have tapered peripheries as shown in FIG. 30, a wire mesh insert 86 similar to the insert 62, can be used to back up the disk layer 82, thereby forming a needle stop area at any actual or potential gaps between the small metal disks 84. The layer 82 and the wire mesh insert 86 thus form a needle impenetrable needle stop barrier 87.

The disk layer 82 and the wire mesh insert 86 are covered with layers 88 and 90 of a suitable elastomeric material such as silicone elastomer. Although not shown, a bead similar to the bead 68 is formed at the periphery of the needle stop 80.

The flexible needle stop 80 can be freely disposed or otherwise incorporated in a tissue expander (not shown) such as the tissue expander 10 or 72. If desired, the needle stop 80 can have a modified bead provided on only one of the layers 88,90, to permit bonding of the other layer to a base surface of the tissue expander. As another option, the needle stop barrier 87 can be incorporated within the base of a tissue expander in the manner shown in FIG. 10. In employing the option of FIG. 10, the disk layer 82 and the wire mesh insert 86 would be incorporated between inner and outer layers 20 and 22 (FIG. 8) of the shell 12. The flexible needle stop 80 and the modifications described herein can thus be used in a manner similar to that previously described for the needle stops 30 and 60.

A flexible needle stop incorporating another embodiment of the invention is generally indicated by the reference number 92 in FIG. 19. The needle stop 92 differs from the needle stop 80 of FIG. 18 by inclusion of an additional layer 94 of disks 84. The disks 84 of layer 94 are offset from the disks 84 of the layer 82 to occupy any actual or potential spaces between disks 84 in the manner shown in FIG. 21. If desired, the disks 84 can be beveled and arranged as shown in FIG. 30.

A wire mesh insert 96 identical to the wire mesh insert 86 can also be incorporated in the needle stop 92 as a further backup to the disk layers 92 and 94. The wire mesh insert 96 can be disposed in direct contact with the disk layer 94 or be separated therefrom by an additional layer 98 of elastomeric material.

The needle stop 92 can be provided with a peripheral bead (not shown) similar to the bead 68 and be freely disposed in a tissue expander (not shown) such as the tissue expander 10 or 72. As another option, the disk layers 82 and 94 and the wire mesh insert 96 can be incorporated in the shell structure of the tissue expander in a manner similar to that shown in FIG. 10 for the needle stop 30.

The needle stop 92 is used in a manner similar to that previously described for the needle stop 80. Flexibility of the needle stop 92 is assured by virtue of the lack of any physical connection between adjacent disks 84 in each of the layers 82 and 94. The needle stop 90 is also foldable and sufficiently flexible to be restorable to an unfolded condition in the manner described with respect to the needle stop 80.

A flexible needle stop incorporating still another embodiment of the invention is generally indicated by the reference number 100 in FIG. 22. The needle stop 100 includes a layer 102 of relatively small scale-like members or disks 104 and a layer 106 of relatively large scale-like members or disks 108. The disk layers 102 and 106 are sandwiched between layers of elastomeric material 110 and 112 similar to the layers 88 and 90 of the needle stops 80 and 92.

The relatively large disks 108 bridge the space between the relatively small disks 104 and the relatively small disks bridge the space between the relatively large disks 108. There is no attachment between the disks 104 or between the disks 108, and the layers 102 and 106 are not attached. If desired, the disks 104 and 108 can be beveled in the same manner as the disks 84 of FIG. 30. Thus a flexible, needle impenetrable needle stop barrier is formed by the disk layers 102 and 106.

The flexible needle stop 100, with a peripheral bead (not shown) similar to the bead 68, can be freely disposed in a tissue expander (not shown) such as the tissue expander 10 or 72. As another option, the layers 102 and 106 can be incorporated in the shell structure of the tissue expander in the manner shown in FIG. 10. The flexible needle stop 100 is used in a manner similar to that previously described for the needle stops 80 and 92. Since a needle impenetrable needle barrier is provided by the disk layers 102 and 106, the inclusion of a wire mesh insert of the type shown in the needle stops 80 and 92 is optional.

Figure 23:
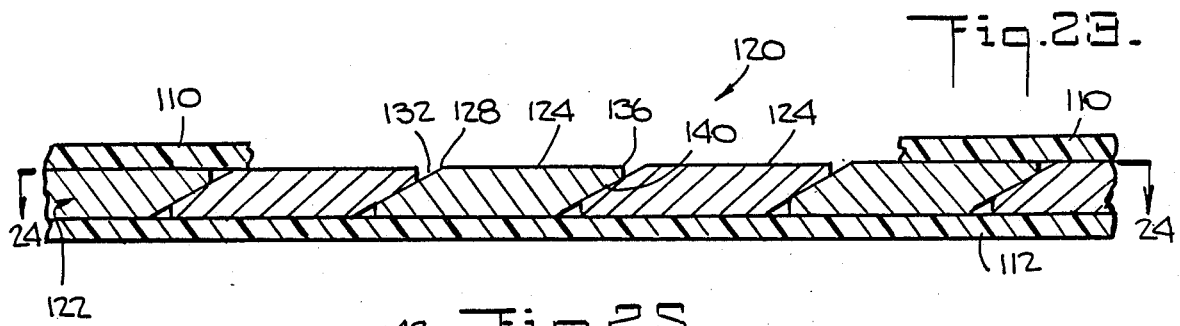
FIG. 23 is a sectional view of a further embodiment of the flexible needle stop.

A flexible needle stop incorporating another embodiment of the invention is generally indicated by the reference number 120 in FIG. 23.

Figure 24:
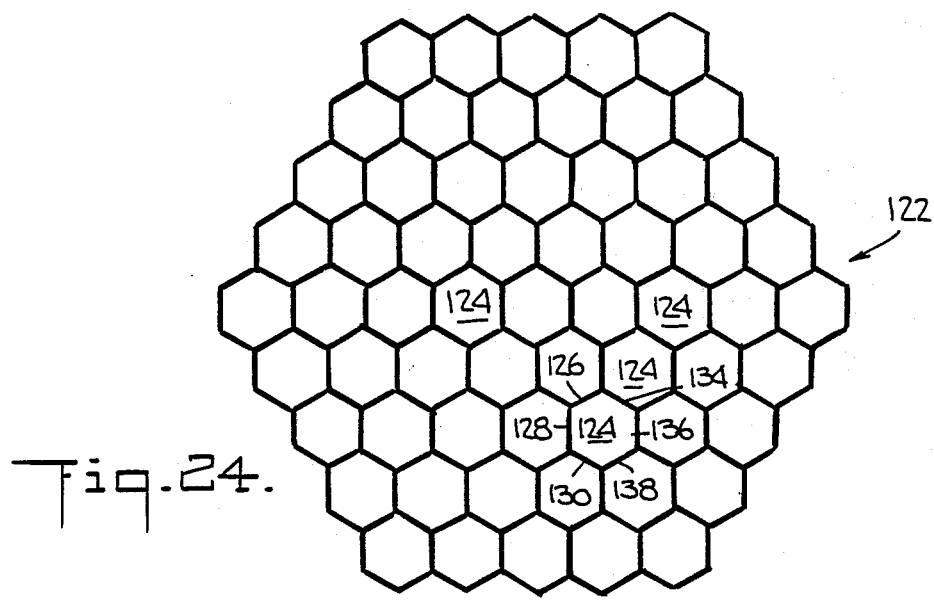
FIG. 24 is a sectional view thereof taken on the line 24—24 of FIG. 23.

The needle stop 120 includes a needle barrier layer 122 formed of a plurality of scale-like members such as hexagonal-shaped disks 124 in a side-by-side abutting relationship. There is no attachment between the disks 124 to assure flexibility of the barrier layer 122. To further assure that a needle (not shown) cannot penetrate between the adjacent hexagonal disks 124, three sides 126, 128 and 130 (FIG. 24) of each disk 124 can be provided with an outward bevel or taper 132 (FIG. 23) and three sides 134, 136 and 138 (FIG. 24) can be provided with an inward bevel or taper 140 (FIG. 23). The adjacent hexagonal disks 124 thus overlap one another in the manner shown in FIG. 23 without being firmly affixed to one another.

The layer 122 of hexagonal disks can be sandwiched between layers of elastomeric material 110 and 112, and provided with a peripheral bead (not shown) similar to the bead 68 for free disposition in a tissue expander such as 10 or 72. If desired, a wire mesh layer (not shown) can also be used to back up the layer 122. Although not shown, as an alternative option, the layer 122 and the wire mesh layer can be incorporated in the shell of the tissue expander in the manner shown in FIG. 10. The needle stop 92 is used in a manner similar to that previously described for the needle stops 80 and 92.

Figure 25:
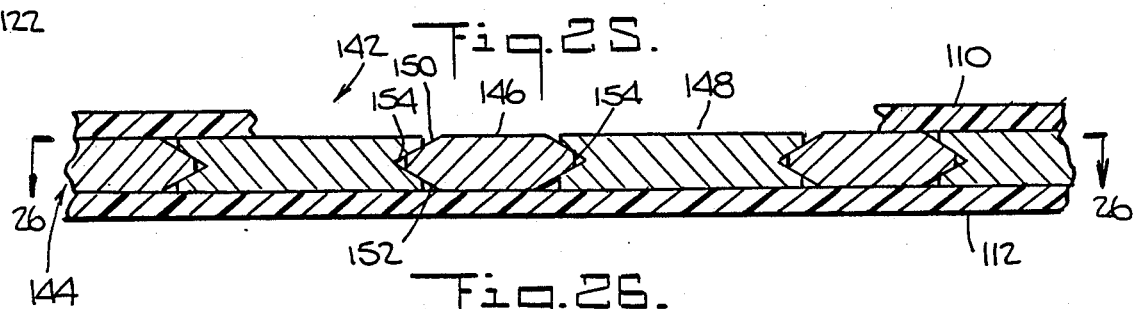
FIG. 25 is a sectional view of a still further embodiment of the flexible needle stop.
Figure 26:
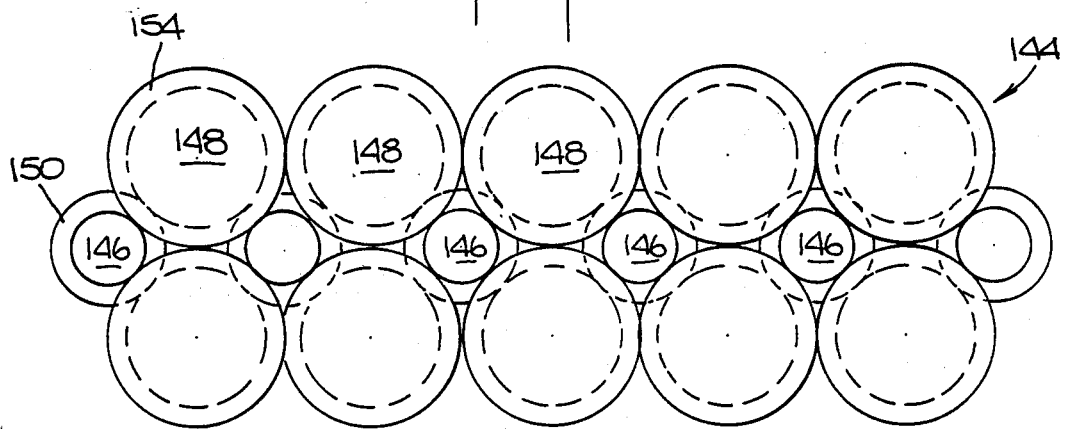
FIG. 26 is a plan view thereof taken on the line 26—26 of FIG. 25.
Figure 28:
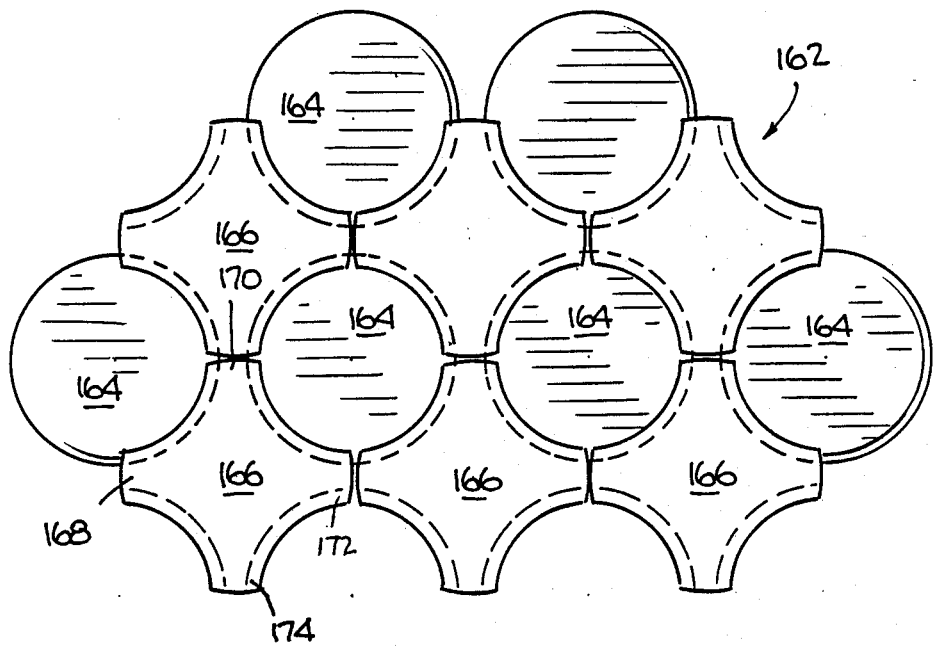
FIG. 28 is a plan view taken on the line 28—28 of FIG. 27.

A flexible needle stop incorporating a still further embodiment of the invention is generally indicated by the reference number 142 in FIG. 25. The needle stop 142 includes a barrier layer 144 of unattached scale-like members such as circular disks 146 and 148 of different size. Referring to FIGS. 25 and 26, the edges of the disks 146 are beveled or tapered at 150 and 152, and the edges of the disk 148 have complementary shaped recesses 154. The tapered portions 150, 152 of the disks 146 can thus engage the recesses 154 of the disks 148 to substantially reduce actual or potential gaps between the disks 146 and 148. To eliminate the possibility that a needle can penetrate and pass beyond the disks 146 and 148, a wire mesh layer (not shown) similar to the layer 62 can be used to back up the layer 144. The barrier layer 144 and wire mesh layer are sandwiched between layers 110 and 112 of elastomeric material and provided with a peripheral bead (not shown) similar to the bead 68 for free disposition in a tissue expander such as 10 or 72. Although not shown, as a further option, the layer 144 and the wire mesh layer (not shown) can be incorporated in the shell of the tissue expander in the manner shown in FIG. 10. The flexible needle stop 140 is used in a manner similar to that previously described for the needle stops 80 and 92.

Figure 27:
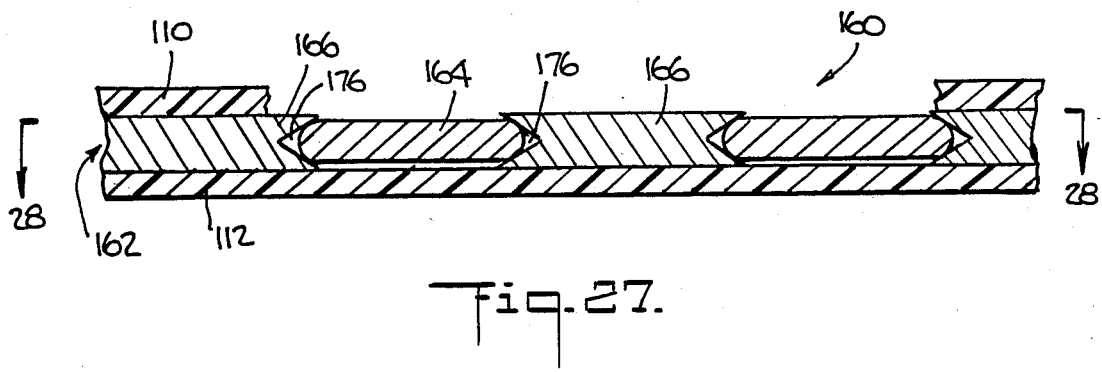
FIG. 27 is a sectional view of a further embodiment of the flexible needle stop.
Figure 29:
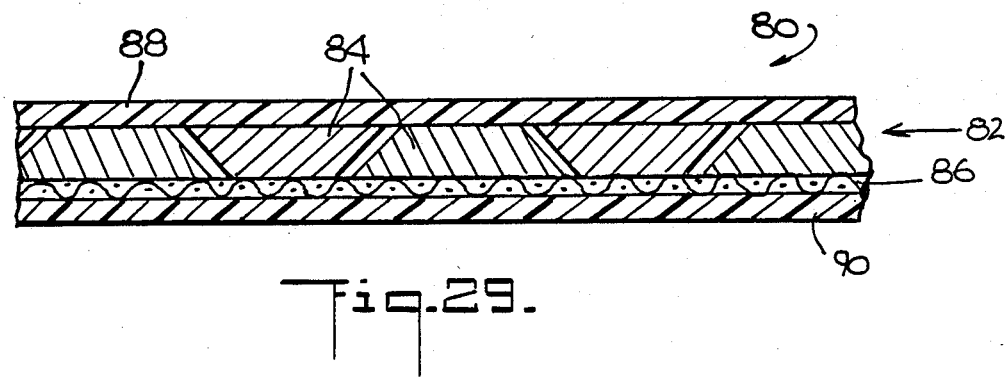
FIG. 29 is an optional modification of the structure shown in FIG. 18.

A flexible needle stop incorporating another embodiment of the invention is generally indicated by the reference number 160 in FIG. 27. The needle stop 160 includes a barrier layer 162 of different shaped scale-like members including a circular-shaped disk 164 and a star-shaped member 166. The star-shaped member 166 includes four projecting arms 168, 170, 172 and 174 having peripheral recesses 176. The recesses 176 accommodate the peripheries of the circular-shaped disks 164. Although not shown, a layer of wire mesh such as the wire mesh 62, can be provided to back up the layer 162.

The barrier layer 162 is sandwiched between elastomeric layers 110 and 112 and provided with a peripheral bead (not shown) similar to the bead 68 for free disposition in a tissue expander such as 10 or 72. Although not shown, a wire mesh layer such as the layer 62, can be used to back up the layer 162. As an alternative option, the layer 162 and the wire mesh layer (not shown) can be incorporated in the shell of the tissue expander in the manner shown in FIG. 10. The needle stop 160 is used in a manner similar to that previously described for the needle stops 80 and 92.

Some advantages of the present invention evident from the foregoing description include a flexible needle stop that can be folded along with a tissue expander in which the needle stop is disposed. The foldability of the needle stop assures that the tissue expander can be compacted to the smallest practical size for implantation in a patient. Due to the small size of the implantation package, the smallest possible implantation incision can be used, thereby minimizing patient discomfort and abbreviating the necessary healing time for such implantation.

A further advantage of the flexible needle stop is that it can be freely disposed in a tissue expander, attached to an interior surface of the fill chamber or incorporated in a wall of the tissue expander.

In view of the above, it will be seen that the several objects of the invention are achieved and other advantageous results attained.

As various changes can be made in the above constructions and method without departing from the scope of the invention, it is intended that all matter contained in the above description or shown in the accompanying drawings shall be interpreted as illustrative and not in a limiting sense.

What is claimed is:

1. An implantable prosthesis comprising:
   a. a tissue expander shell defining an internal chamber infusible with fluid, said shell being substantially flexible and substantially foldable when said chamber is substantially empty, said shell having a needle penetrable portion for permitting entry of an infusion needle into said internal chamber for infusion of fluid in said internal chamber,
   b. a needle impenetrable needle stop disposed within said shell, said needle stop having a predetermined shape and size, and a normally unfolded condition, said needle stop being flexible and foldable to permit manual flexion and folding of said needle stop and said shell when said internal chamber is substantially empty, said needle stop being positioned within said shell in a predetermined orientation with respect to said shell to stop said infusion needle from progressing in a predetermined direction outwardly of said shell after said infusion needle has entered said internal chamber.

2. An implantable prosthesis as claimed in claim 1 wherein said shell includes a shell wall and said needle stop is sandwiched within a predetermined section of said shell wall.

3. An implantable prosthesis as claimed in claim 1 wherein said shell has an interior surface inside said chamber and said needle stop is adhered to a predetermined portion of said interior surface.

4. An implantable prosthesis as claimed in claim 1 wherein said needle stop is covered with an elastomeric material.

5. An implantable prosthesis as claimed in claim 4 wherein sad shell has an interior surface inside said chamber and said needle stop is adhered to a predetermined portion of said interior surface.

6. An implantable prosthesis as claimed in claim 1 wherein said needle stop is disposed in said internal chamber without affixation to said shell.

7. An implantable prosthesis as claimed in claim 1 wherein said needle stop has a shape and surface contour substantially corresponding to the shape and surface contour of a predetermined section of said shell, said needle stop being formed of a needle impenetrable material having a normally unfolded configuration.

8. An implantable prosthesis as claimed in claim 7 wherein said needle stop is a one-piece member.

9. An implantable prosthesis as claimed in claim 8 wherein said needle stop has a peripheral edge with a peripheral bead.

10. An implantable prosthesis as claimed in claim 9 wherein said peripheral bead is said peripheral edge rolled upon itself.

11. An implantable prosthesis as claimed in claim 1 wherein said needle stop includes a plurality of separately formed scale-like members of predetermined size and shape arranged substantially side-by-side in a first layer such that selected peripheral portions of adjacent scale-like members are in contact.

12. An implantable prosthesis as claimed in claim 11 wherein said scale-like members include first and second differently shaped scale members arranged to engage peripherally to provide a predetermined repeating pattern of peripheral engagement of said first and second scale members.

13. An implantable prosthesis as claimed in claim 12 wherein the periphery of at least one of said first and second differently shaped scale members projects into the periphery of the other said scale member to eliminate needle penetrable spaces between said engaged portions.

14. An implantable prosthesis as claimed in claim 12 wherein a side portion of one of said first and second differently shaped scale members engage a corresponding side portion of another of said one scale members.

15. An implantable prosthesis as claimed in claim 14 wherein one of said differently shaped scale-like members is a four-pronged star with radially consecutive prongs and concave circular arcs between said radially consecutive prongs, and the other of said differently shaped scale-like members is of circular periphery, said circular scale-like member and the concave circular arcs of said four-pronged star being of complimentary size and shape to permit engagement between the concave circular arcs of said one of said scale members and the circular periphery of the other said scale member.

16. An implantable prosthesis as claimed in claim 15 wherein one of said concave circular arc and circular periphery contours is formed with peripheral grooves and the other of said contours is formed with peripheral groove engaging portions, said first and second scale-like members being arranged to provide peripheral engagement between the respective grooves and the groove engaging portions to eliminate needle penetrable spaces between said engaged contours.

17. An implantable prosthesis as claimed in claim 11 wherein said needle stop includes a layer of flexible, foldable, needle-impenetrable mesh material.

18. An implantable prosthesis as claimed in claim 11 including a second layer of said scale-like members disposed on said first layer.

19. An implantable prosthesis as claimed in claim 18 wherein the scale-like members in said first and second layers are of corresponding size and shape.

20. An implantable prosthesis as claimed in claim 18 wherein the scale-like members in said second layer are offset from the scale-like members in said first layer.

21. An implantable prosthesis as claimed in claim 18 wherein said scale-like members in one of said layers are of different size than the scale-like members in the other said layer.

22. An implantable prosthesis as claimed in claim 18 wherein the scale-like members in one of said layers are of different shape than the scale-like members in the other said layer.

23. An implantable prosthesis as claimed in claim 11 wherein said scale-like members are of circular shape.

24. An implantable prosthesis as claimed in claim 11 wherein said scale-like members are of polygonal shape.

25. An implantable prosthesis as claimed in claim 24 wherein said scale-like members are of hexagonal shape.

26. An implantable prosthesis as claimed in claim 11 wherein a first portion of said scale-like members have peripheral grooves and a second portion of said scale-like members have peripheral groove engaging forms, said first and second portions of said scale-like members being arranged to provide peripheral engagement between the respective grooves and the respective groove engaging portions.

27. An implantable prosthesis as claimed in claim 11 wherein a first predetermined peripheral portion of said scale-like members have a first bevel and a second predetermined peripheral portion of said scale-like members have a second bevel, said first and second bevels being complimentary such that there is predetermined peripheral overlap between adjacent scale-like members.

28. An implantable prosthesis as claimed in claim 1 wherein said needle stop has a predetermined resiliency that enables said needle stop to reassume said unfolded condition after it has been manually folded and the manual folding force is removed from the needle stop.

29. An implantable prosthesis as claimed in claim 1 wherein said shell is self sealing at said needle penetrable portion after said infusion needle is withdrawn from said needle penetrable portion.

30. An implantable prosthesis as claimed in claim 1 wherein said needle stop includes a layer of flexible, foldable, needle-impenetrable mesh material.

31. An implantable prosthesis as claimed in claim 1 wherein said needle stop has a peripheral edge with a peripheral bead.

32. An implantable prosthesis as claimed in claim 1 wherein said needle stop has a peripheral fold.

33. An implantable prosthesis as claimed in claim 4 wherein said elastomeric material includes at least one layer formed with a rib-like reinforcement to promote quick return of the needle stop to a flat position after being folded.

34. An implantable prosthesis as claimed in claim 4 wherein said elastomeric material includes at least one layer formed with at least one groove to enhance foldability of said needle stop along said groove.

35. A method of expanding tissue comprising:
   a. forming a shell to define an internal chamber to be infused with fluid,
   b. rendering the shell flexible and foldable when the internal chamber is substantially empty,
   c. installing a normally unfolded needle impenetrable needle stop within the shell,
   d. rendering the needle stop flexible and foldable to permit folding and flexing of the shell at the area of the needle stop when the chamber is substantially empty,
   e. folding the shell and needle stop to reduce the overall size of the prosthesis before implantation to a size that is smaller than the size of the unfolded shell,
   f. implanting the prosthesis through an incision corresponding to the size of the folded prosthesis, and
   g. expanding the prosthesis to its unfolded size after it has been implanted.

36. The method of claim 35 including, orienting the shell such that the needle stop is at a proximal location in the shell and passing an infusion needle through a distal portion of the shell such that the needle is prevented from progressing out of the infusion chamber by the needle stop.

* * * * *